United States Patent [19]
Van Solingen

[11] Patent Number: 6,063,611
[45] Date of Patent: May 16, 2000

[54] ALKALINE CELLULASE AND METHOD OF PRODUCING SAME

[75] Inventor: Pieter Van Solingen, Naaldwijk, Netherlands

[73] Assignee: Genencor International, Inc., Rochester, N.Y.

[21] Appl. No.: 08/732,433

[22] PCT Filed: Apr. 26, 1996

[86] PCT No.: PCT/US96/05651

§ 371 Date: Apr. 18, 1997

§ 102(e) Date: Apr. 18, 1997

[87] PCT Pub. No.: WO97/34005

PCT Pub. Date: Sep. 18, 1997

Related U.S. Application Data

[63] Continuation of application No. 08/614,115, Mar. 12, 1996, abandoned.

[51] Int. Cl.[7] .............................. C12N 9/42; D06M 16/00; D21C 3/00; C11D 3/00

[52] U.S. Cl. .......................... 435/209; 435/263; 435/277; 435/278; 435/320.1; 510/300; 510/320; 514/44; 544/733

[58] Field of Search ................................. 435/209, 320.1, 435/263, 277, 278; 424/94.61; 514/44; 536/23.2; 510/320, 300; 524/733; 544/733

[56] References Cited

FOREIGN PATENT DOCUMENTS

91/10732  7/1991  WIPO .
95/18219  7/1995  WIPO .

*Primary Examiner*—Bradley L. Sisson
*Assistant Examiner*—Einar Stole
*Attorney, Agent, or Firm*—Christopher L. Stone; Susan Faris

[57] ABSTRACT

The present invention provides a novel cellulase composition obtainable from Bacillus sp. CBS 669.93. A preferred cellulase has a calculated molecular weight of approximately 63 kD, a calculated isoelectric point of about 5 and a pH optimum on CMC of about 6 at 40° C. and 60° C.

9 Claims, 4 Drawing Sheets

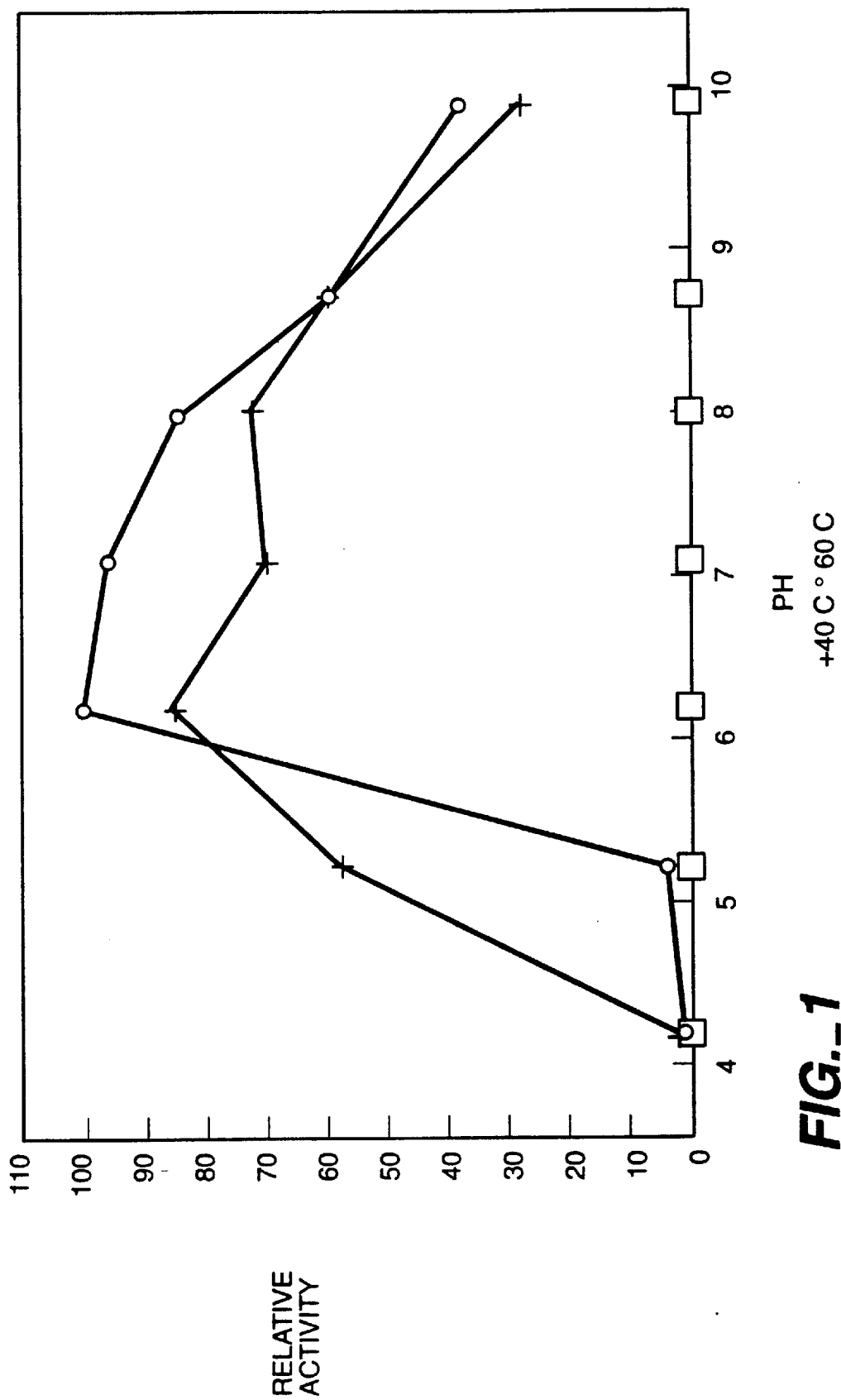
FIG._1

```
-630                              GAATTCTTTGGATCATGATGGAAGGCGAAA

-600  TCATGAGCATTGCCCTTGCGACGATTACGGCTTCTGTCGGCGTCTACTTGCTTGCGTCAG

-540  CGGTTCAAGGTTGGTTTGCAGGTAAAGCTGCATTAACTGTTGTTCGTTTACTTCTCATTG

-480  TCGCTGCTGTTTGTCTTATTCATTCAAATTGGGTGTATGACTTTGTCGCCCTCGGNATCG

-420  CGGGTATCGCCATTATNCTTCAAAGAACAGTTATTAACAGACGCCATGGGTTCCAAGGCA

-360  AGTACAGTTTAAAACGAGAGATTTAAGAGGCCGCTCCCAATGAGGGAGTGGTCTTTTTTA

-300  CATTCNAAAAGAGGAAAATAGGAGAAATGTAGATCCGACGTAGATAAGTATTAGGTTTT

-240  AAGTGTAAGTACAGCTAAGAAAGCTGCTTTTGCTGATTCTATGAAAAAGTGCTTGTTAAA

-180  CATTTTGACATGATTTTCTGTGAAATAAATGATCTATTTTCTGTGAAACAATTGTGATAG

-120  ATTGGTGTAGAGTTTTGATAATTCTAAATTTTCGTTCAAAAGGAGGTTGAGGTTCATTTA

-60  CGATTTTGTCAACAGTCAATTGTTGTTTCCGGGTAACTCATTTGGAGGTGGTGGAGTCTG

1  ATGAAGTGGATGAAATCCATGGTATGGTTGGCCGTTGTTTTGGTCGTTTCGTTCGTAGCT
      MetLysTrpMetLysSerMetValTrpLeuAlaValValLeuValValSerPheValAla

61  CCTGCCGTTAGTTCAGCTAATGAGGATGTAAAAACTCTCGATATTCAGTCCTATGTAAGA
      ProAlaValSerSerAlaAsnGluAspValLysThrLeuAspIleGlnSerTyrValArg

121  GACATGCAGCCGGGTTGGAATCTTGGGAATACGTTTGATGCCGTCGGACAAGATGAAACA
      AspMetGlnProGlyTrpAsnLeuGlyAsnThrPheAspAlaValGlyGlnAspGluThr

181  GCATGGGGAAATCCACGTGTGACACGAGAATTAATTGAACGGATTGCGGATGAAGGGTAT
      AlaTrpGlyAsnProArgValThrArgGluLeuIleGluArgIleAlaAspGluGlyTyr

241  AAAAGCATTCGGATTCCGGTGACGTGGGAAAATCGTATCGGAGGGGCACCTGATTATCCT
      LysSerIleArgIleProValThrTrpGluAsnArgIleGlyGlyAlaProAspTyrPro

301  ATTGATCCCCAGTTTTTAAATCGAGTGGACGAAGTTGTTCAATGGGCGCTGGAAGAAGAT
      IleAspProGlnPheLeuAsnArgValAspGluValValGlnTrpAlaLeuGluGluAsp

361  TTGTATGTCATGATTAATTTACACCATGATTCATGGTTATGGATTTATGAAATGGAGCAC
      LeuTyrValMetIleAsnLeuHisHisAspSerTrpLeuTrpIleTyrGluMetGluHis

421  AACTACAACGGTGTGATGGCCAAGTATCGCTCGCTCTGGGAGCAACTATCGAACCACTTC
      AsnTyrAsnGlyValMetAlaLysTyrArgSerLeuTrpGluGlnLeuSerAsnHisPhe

481  AAAGACTATCCAACAAAGCTTATGTTTGAAAGTGTCAATGAGCCAAAGTTTAGTCAAAAC
      LysAspTyrProThrLysLeuMetPheGluSerValAsnGluProLysPheSerGlnAsn

541  TGGGGTGAGATCCGTGAGAATCACCATGCGTTACTAGACGACTTAAACACAGTGTTTTTC
      TrpGlyGluIleArgGluAsnHisHisAlaLeuLeuAspAspLeuAsnThrValPhePhe

601  GAGATTGTGAGACAGTCTGGTGGCCAAAATGATATCCGGCCGTTAGTGTTACCGACTATG
      GluIleValArgGlnSerGlyGlyGlnAsnAspIleArgProLeuValLeuProThrMet

661  GAAACAGCCACATCACAACCGTTGCTGAACAACCTTTATCAAACAATTGACAAATTGGAT
      GluThrAlaThrSerGlnProLeuLeuAsnAsnLeuTyrGlnThrIleAspLysLeuAsp
```

*FIG._2A*

```
 721 GATCCGAATCTAATTGCGACAGTACACTATTACGGGTTTTGGCCTTTTAGCGTGAATATC
     AspProAsnLeuIleAlaThrValHisTyrTyrGlyPheTrpProPheSerValAsnIle

781 GCCGGCTACACTCGCTTTGAAGAGGATTCGAAACGGGAGATCATCGAAACGTTTGATCGA
     AlaGlyTyrThrArgPheGluGluAspSerLysArgGluIleIleGluThrPheAspArg

841 GTACACCATACATTTGTTGCAAGAGGGATTCCAGTCGTTTTAGGTGAGTTCGGCTTGCTT
     ValHisHisThrPheValAlaArgGlyIleProValValLeuGlyGluPheGlyLeuLeu

901 GGATTTGATAAACATACTGGAGTGATTCAACAAGGTGAAAAGCTAAAATTCTTTGAGTAT
     GlyPheAspLysHisThrGlyValIleGlnGlnGlyGluLysLeuLysPhePheGluTyr

961 CTCATCCATCATTTGAACGAGCGGGATATTACTCATATGCTTTGGGATAATGGGCAGCAT
     LeuIleHisHisLeuAsnGluArgAspIleThrHisMetLeuTrpAspAsnGlyGlnHis

1021 TTCAATCGTCATACGTACGAATGGTATGACGAGGAATTGTTTGACATGTTGCGGGCAAGC
     PheAsnArgHisThrTyrGluTrpTyrAspGluGluLeuPheAspMetLeuArgAlaSer

1081 TGGGGAGGAAGATCATCCGTTGCAGAGTCGAACTTTATCTATTTAAAACAGGGAGACCGA
     TrpGlyGlyArgSerSerValAlaGluSerAsnPheIleTyrLeuLysGlnGlyAspArg

1141 ATCGCAGATGCAACAGTTACATTACAATTGCACGGAAATGAATTAACAGGGCTTCAGGCG
     IleAlaAspAlaThrValThrLeuGlnLeuHisGlyAsnGluLeuThrGlyLeuGlnAla

1201 AATGGACAACGACTAACGCCGGGGCAGGACTATGAGTTAAATGGAGAAAGACTTACAGTG
     AsnGlyGlnArgLeuThrProGlyGlnAspTyrGluLeuAsnGlyGluArgLeuThrVal

1261 AAGGCCCATGTCCTATCGGCAATCGCAGGTTCAGGTACGTTAGGTACGAATGGAATGGTA
     LysAlaHisValLeuSerAlaIleAlaGlySerGlyThrLeuGlyThrAsnGlyMetVal

1321 ACGGCTGAGTTTAATCGTGGGGCAGATTGGCATTTTCGGGTGAATACGTATCGTACGCCT
     ThrAlaGluPheAsnArgGlyAlaAspTrpHisPheArgValAsnThrTyrArgThrPro

1381 GTATTGCAAAGCACGCAAGGTCACGTGAGCAACTTCAGCATTCCTGCTTCCTTTAATGGG
     ValLeuGlnSerThrGlnGlyHisValSerAsnPheSerIleProAlaSerPheAsnGly

1441 AATAGCTTAGCAACAATGGAGGCTGTCTATGTGGATGGCGGAAATGCTGGCCCGCAAGAC
     AsnSerLeuAlaThrMetGluAlaValTyrValAspGlyGlyAsnAlaGlyProGlnAsp

1501 TGGACCTCCTTTAAGGAGTTTGGCTATGCCTTCTCTCCTTCTTATGATACACATGAGATT
     TrpThrSerPheLysGluPheGlyTyrAlaPheSerProSerTyrAspThrHisGluIle

1561 AAACTGACCGAGGCGTTTTTTCGTGAGGTGCGGGATGGTGAAGTTCGGTTAACCTTCCAT
     LysLeuThrGluAlaPhePheArgGluValArgAspGlyGluValArgLeuThrPheHis

1621 TTTTGGAGTGGTGAAATAGTCAACTATACGATTATTAAAAACGGGAACCAGGTGACTGGG
     PheTrpSerGlyGluIleValAsnTyrThrIleIleLysAsnGlyAsnGlnValThrGly

1681 ATAGCAGCTCAGACAACCAATTCAAAAAACAAAAATAAAAAATGAAATTGAAAGCGCTTT
     IleAlaAlaGlnThrThrAsnSerLysAsnLysAsnLysLysEnd

1741 CTATGGTGTTGCCCGAATATCTGAGGTTCTTTAGTAGAATCCGATATTCGGGTTTTTTCA

1801 TACATTATAGGGGCGCTTTTTTATGTTGCGCAGGTTAAATGGTCTTACGTATGGGAACCC

1861 TACTACTAGATTATTGTGCACTCTTTTTGAGTACCATTATCACCGCCCTATCATATGTAT
```

FIG._2B

```
1921 ATGAGTTGAACCATCTAGTAACCTCTCTTAAAATTGGTAAAGGAAATGTAACGTTGTGAT

2041 AGTAAGGAAATGGTATGATGGAGAGAGACGTGTGATCGAGAAATGGAGGAACGCAGAATG

2101 AATGAAACGATGCAACGCATCGCGAGAGTCATAGAGAATGTGGAACGAGTGGCCGCCGGG

2161 AAACGTCAGGAAATCGAGCTGAGCCTTGTCGCATTATTTGCTAGCGG
```

FIG._2C

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 574 amino acids
      (B) TYPE: amino acid
      (C) STRANDEDNESS: single
      (D) TOPOLOGY: linear (xi) SEQUENCE DESCRIPTION: SEQ ID NO:1:

```
Met Lys Trp Met Lys Ser Met Val Trp Leu Ala Val Leu Val Val
 1               5                  10                  15

Ser Phe Val Ala Pro Ala Val Ser Ser Ala Asn Glu Asp Val Lys Thr
                 20                  25                  30

Leu Asp Ile Gln Ser Tyr Val Arg Asp Met Gln Pro Gly Trp Asn Leu
             35                  40                  45

Gly Asn Thr Phe Asp Ala Val Gly Gln Asp Glu Thr Ala Trp Gly Asn
     50                  55                  60

Pro Arg Val Thr Arg Glu Leu Ile Glu Arg Ile Ala Asp Glu Gly Tyr
 65              70                  75                  80

Lys Ser Ile Arg Ile Pro Val Thr Trp Glu Asn Arg Ile Gly Gly Ala
                 85                  90                  95

Pro Asp Tyr Pro Ile Asp Pro Gln Phe Leu Asn Arg Val Asp Glu Val
                100                 105                 110

Val Gln Trp Ala Leu Glu Glu Asp Leu Tyr Val Met Ile Asn Leu His
         115                 120                 125

His Asp Ser Trp Leu Trp Ile Tyr Glu Met Glu His Asn Tyr Asn Gly
    130                 135                 140

Val Met Ala Lys Tyr Arg Ser Leu Trp Glu Gln Leu Ser Asn His Phe
145                 150                 155                 160

Lys Asp Tyr Pro Thr Lys Leu Met Phe Glu Ser Val Asn Glu Pro Lys
                165                 170                 175

Phe Ser Gln Asn Trp Gly Glu Ile Arg Glu Asn His His Ala Leu Leu
            180                 185                 190

Asp Asp Leu Asn Thr Val Phe Phe Glu Ile Val Arg Gln Ser Gly Gly
        195                 200                 205

Gln Asn Asp Ile Arg Pro Leu Val Leu Pro Thr Met Glu Thr Ala Thr
    210                 215                 220

Ser Gln Pro Leu Leu Asn Asn Leu Tyr Gln Thr Ile Asp Lys Leu Asp
225                 230                 235                 240

Asp Pro Asn Leu Ile Ala Thr Val His Tyr Tyr Gly Phe Trp Pro Phe
                245                 250                 255

Ser Val Asn Ile Ala Gly Tyr Thr Arg Phe Glu Glu Asp Ser Lys Arg
            260                 265                 270

Glu Ile Ile Glu Thr Phe Asp Arg Val His His Thr Phe Val Ala Arg
        275                 280                 285

Gly Ile Pro Val Val Leu Gly Glu Phe Gly Leu Leu Gly Phe Asp Lys
    290                 295                 300

His Thr Gly Val Ile Gln Gln Gly Glu Lys Leu Lys Phe Glu Tyr
305                 310                 315                 320

Leu Ile His His Leu Asn Glu Arg Asp Ile Thr His Met Leu Trp Asp
                325                 330                 335

Asn Gly Gln His Phe Asn Arg His Thr Tyr Glu Trp Tyr Asp Glu Glu
            340                 345                 350

Leu Phe Asp Met Leu Arg Ala Ser Trp Gly Gly Arg Ser Ser Val Ala
        355                 360                 365

Glu Ser Asn Phe Ile Tyr Leu Lys Gln Gly Asp Arg Ile Ala Asp Ala
    370                 375                 380

Thr Val Thr Leu Gln Leu His Gly Asn Glu Leu Thr Gly Leu Gln Ala
385                 390                 395                 400

Asn Gly Gln Arg Leu Thr Pro Gly Gln Asp Tyr Glu Leu Asn Gly Glu
```

```
                    405                 410                 415
Arg Leu Thr Val Lys Ala His Val Leu Ser Ala Ile Ala Gly Ser Gly
                420                 425                 430

Thr Leu Gly Thr Asn Gly Met Val Thr Ala Glu Phe Asn Arg Gly Ala
            435                 440                 445

Asp Trp His Phe Arg Val Asn Thr Tyr Arg Thr Pro Val Leu Gln Ser
        450                 455                 460

Thr Gln Gly His Val Ser Asn Phe Ser Ile Pro Ala Ser Phe Asn Gly
465                 470                 475                 480

Asn Ser Leu Ala Thr Met Glu Ala Val Tyr Val Asp Gly Gly Asn Ala
                485                 490                 495

Gly Pro Gln Asp Trp Thr Ser Phe Lys Glu Phe Gly Tyr Ala Phe Ser
                500                 505                 510

Pro Ser Tyr Asp Thr His Glu Ile Lys Leu Thr Glu Ala Phe Phe Arg
            515                 520                 525

Glu Val Arg Asp Gly Glu Val Arg Leu Thr Phe His Phe Trp Ser Gly
        530                 535                 540

Glu Ile Val Asn Tyr Thr Ile Ile Lys Asn Gly Asn Gln Val Thr Gly
545                 550                 555                 560

Ile Ala Ala Gln Thr Thr Asn Ser Lys Asn Lys Asn Lys Lys
                565                 570
```

(2) INFORMATION FOR SEQ ID NO:2:

(i) SEQUENCE CHARACTERISTICS:
        (A) LENGTH: 2774 base pairs
        (B) TYPE: nucleic acid
        (C) STRANDEDNESS: single
        (D) TOPOLOGY: linear (xi) SEQUENCE DESCRIPTION: SEQ ID NO:2:

```
GAATTCTTTG GATCATGATG AAGGCGAAA TCATGAGCAT TGCCCTTGCG ACGATTACGG        60

CTTCTGTCGG CGTCTACTTG CTTGCGTCAG CGGTTCAAGG TTGGTTTGCA GGTAAAGCTG      120

CATTAACTGT TGTTCGTTTA CTTCTCATTG TCGCTGCTGT TTGTCTTATT CATTCAAATT      180

GGGTGTATGA CTTTGTCGCC CTCGGATCGC GGGTATCGCC ATTATCTTCA AAGAACAGTT      240

ATTAACAGAC GCCATGGGTT CCAAGGCAAG TACAGTTTAA AACGAGAGAT TTAAGAGGCC      300

GCTCCCAATG AGGGAGTGGT CTTTTTTACA TTCAAAAAGA GGAAAATAGG AGAAATGTAG      360

ATCCGACGTA GATAAGTATT AGGTTTTAAG TGTAAGTACA GCTAAGAAAG CTGCTTTTGC      420

TGATTCTATG AAAAAGTGCT TGTTAAACAT TTTGACATGA TTTTCTGTGA AATAAATGAT      480

CTATTTTCTG TGAAACAATT GTGATAGATT GGTGTAGAGT TTTGATAATT CTAAATTTTC      540

GTTCAAAAGG AGGTTGAGGT TCATTTACGA TTTTGTCAAC AGTCAATTGT TGTTTCCGGG      600

TAACTCATTT GGAGGTGGTG GAGTCTGATG AAGTGGATGA AATCCATGGT ATGGTTGGCC      660

GTTGTTTTGG TCGTTTCGTT CGTAGCTCCT GCCGTTAGTT CAGCTAATGA GGATGTAAAA      720

ACTCTCGATA TTCAGTCCTA TGTAAGAGAC ATGCAGCCGG TTGGAATCT TGGGAATACG       780

TTTGATGCCG TCGGACAAGA TGAAACAGCA TGGGGAAATC CACGTGTGAC ACGAGAATTA     840

ATTGAACGGA TTGCGGATGA AGGGTATAAA AGCATTCGGA TTCCGGTGAC GTGGGAAAAT     900

CGTATCGGAG GGGCACCTGA TTATCCTATT GATCCCCAGT TTTTAAATCG AGTGGACGAA     960

GTTGTTCAAT GGGCGCTGGA AGAAGATTTG TATGTCATGA TTAATTTACA CCATGATTCA    1020

TGGTTATGGA TTTATGAAAT GGAGCACAAC TACAACGGTG TGATGGCCAA GTATCGCTCG    1080
```

-continued

```
CTCTGGGAGC AACTATCGAA CCACTTCAAA GACTATCCAA CAAAGCTTAT GTTTGAAAGT    1140

GTCAATGAGC CAAAGTTTAG TCAAAACTGG GGTGAGATCC GTGAGAATCA CCATGCGTTA    1200

CTAGACGACT TAAACACAGT GTTTTTCGAG ATTGTGAGAC AGTCTGGTGG CCAAAATGAT    1260

ATCCGGCCGT TAGTGTTACC GACTATGGAA ACAGCCACAT CACAACCGTT GCTGAACAAC    1320

CTTTATCAAA CAATTGACAA ATTGGATGAT CCGAATCTAA TTGCGACAGT ACACTATTAC    1380

GGGTTTTGGC CTTTTAGCGT GAATATCGCC GGCTACACTC GCTTTGAAGA GGATTCGAAA    1440

CGGGAGATCA TCGAAACGTT TGATCGAGTA CACCATACAT TTGTTGCAAG AGGGATTCCA    1500

GTCGTTTTAG GTGAGTTCGG CTTGCTTGGA TTTGATAAAC ATACTGGAGT GATTCAACAA    1560

GGTGAAAAGC TAAAATTCTT TGAGTATCTC ATCCATCATT TGAACGAGCG GGATATTACT    1620

CATATGCTTT GGGATAATGG GCAGCATTTC AATCGTCATA CGTACGAATG GTATGACGAG    1680

GAATTGTTTG ACATGTTGCG GGCAAGCTGG GGAGGAAGAT CATCCGTTGC AGAGTCGAAC    1740

TTTATCTATT TAAAACAGGG AGACCGAATC GCAGATGCAA CAGTTACATT ACAATTGCAC    1800

GGAAATGAAT TAACAGGGCT TCAGGCGAAT GGACAACGAC TAACGCCGGG GCAGGACTAT    1860

GAGTTAAATG GAGAAAGACT TACAGTGAAG GCCCATGTCC TATCGGCAAT CGCAGGTTCA    1920

GGTACGTTAG GTACGAATGG AATGGTAACG GCTGAGTTTA ATCGTGGGGC AGATTGGCAT    1980

TTTCGGGTGA ATACGTATCG TACGCCTGTA TTGCAAAGCA CGCAAGGTCA CGTGAGCAAC    2040

TTCAGCATTC CTGCTTCCTT TAATGGGAAT AGCTTAGCAA CAATGGAGGC TGTCTATGTG    2100

GATGGCGGAA ATGCTGGCCC GCAAGACTGG ACCTCCTTTA AGGAGTTTGG CTATGCCTTC    2160

TCTCCTTCTT ATGATACACA TGAGATTAAA CTGACCGAGG CGTTTTTTCG TGAGGTGCGG    2220

GATGGTGAAG TTCGGTTAAC CTTCCATTTT TGGAGTGGTG AAATAGTCAA CTATACGATT    2280

ATTAAAAACG GAACCAGGT GACTGGGATA GCAGCTCAGA CAACCAATTC AAAAAACAAA    2340

AATAAAAAAT GAAATTGAAA GCGCTTTCTA TGGTGTTGCC CGAATATCTG AGGTTCTTTA    2400

GTAGAATCCG ATATTCGGGT TTTTTCATAC ATTATAGGGG CGCTTTTTTA TGTTGCGCAG    2460

GTTAAATGGT CTTACGTATG GGAACCCTAC TACTAGATTA TTGTGCACTC TTTTTGAGTA    2520

CCATTATCAC CGCCCTATCA TATGTATATG AGTTGAACCA TCTAGTAACC TCTCTTAAAA    2580

TTGGTAAAGG AAATGTAACG TTGTGATAGT AAGGAAATGG TATGATGGAG AGAGACGTGT    2640

GATCGAGAAA TGGAGGAACG CAGAATGAAT GAAACGATGC AACGCATCGC GAGAGTCATA    2700

GAGAATGTGG AACGAGTGGC CGCCGGGAAA CGTCAGGAAA TCGAGCTGAG CCTTGTCGCA    2760

TTATTTGCTA GCGG                                                     2774
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:3:

```
Asn Glu Asp Val Lys Thr Leu Asp Ile Gln
1               5                   10
```

ALKALINE CELLULASE AND METHOD OF PRODUCING SAME

This application is a 371 of PCT/US96/05651, filed Apr. 26, 1996 and a continuation of Ser. No. 08/614,115, filed Mar. 12, 1996.

BACKGROUND OF THE INVENTION

A. Technical Field

The present invention relates to novel cellulase compositions. The invention further relates to novel cellulase compositions, preferably derived from Bacillus sp. The present invention further relates to the use of the novel cellulase in compositions recognized in the art as advantageously having cellulase added thereto, including, as an additive in a detergent composition, in the treatment of cellulose containing fabrics, in the treatment of pulp and paper and in the treatment of starch for the production of high fructose corn-syrup or ethanol.

B. State of the Art

Cellulases are enzymes which are capable of the hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al. (1987), TIBTECH 5, 255–261); and are known to be produced by a large number of bacteria, yeasts and fungi.

Primary among the applications that have been developed for the use of cellulolytic enzymes are those involving degrading (wood)cellulose pulp into sugars for (bio)ethanol production, textile treatments like 'stone washing' and 'biopolishing', and in detergent compositions. Thus, cellulases are known to be useful in detergent compositions for removing dirt, i.e., cleaning. For example, Great Britain Application Nos. 2,075,028, 2,095,275 and 2,094,826 illustrate improved cleaning performance when detergents incorporate cellulase. Additionally, Great Britain Application No. 1,358,599 illustrates the use of cellulase in detergents to reduce the harshness of cotton containing fabrics.

Another useful feature of cellulases in the treatment of textiles is their ability to recondition used fabrics by making their colors more vibrant. For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Despite knowledge in the art related to many cellulase compositions having some or all of the above properties, there is a continued need for new cellulases having a varying spectrum of characteristics which are useful in, for example, treating textiles, as a component of detergent compositions, in the treatment of pulp and paper, and in the conversion of biomass. Applicants have discovered certain cellulases which have such a complement of characteristics and which are useful in such known applications of cellulase.

SUMMARY OF THE INVENTION

It is an object of the present invention to provide a novel cellulase having beneficial properties for use in detergents, treating textiles and pulp and paper manufacturing.

According to the present invention, a cellulase is obtainable from or derived from Bacillus sp. CBS 669.93, or a derivative of said cellulase. CBS 669.93 is deposited at the Centraalbureau voor Schimmelcultures (CBS), Baam, Netherlands under accession number CBS 669.93, on Dec. 23, 1993 ("CBS 669.93"). Preferably, the novel cellulase comprises an amino acid sequence according to FIGS. 2A–2C (SEQ ID NO:1), or a derivative thereof having greater than 58% sequence identity, preferably at least 80% sequence identity and more preferably at least 90% sequence identity thereto. The present invention is also directed to a novel cellulase comprising an amino acid sequence according to FIGS. 2A–2C (SEQ ID NO:1), or a derivative thereof having greater than 72% sequence similarity, preferably at least 80% sequence similarity and most preferably at least 90% sequence similarity.

According to another embodiment, a composition is provided comprising DNA which encodes an amino acid sequence according to FIGS. 2A–2C (SEQ ID NO: 1), or a derivative thereof having greater than 58% sequence identity, preferably 80% sequence identity and more preferably 90% sequence identity thereto. Alternatively, a composition is provided comprising DNA which encodes an amino acid sequence according to FIGS. 2A–2C (SEQ ID NO:1), or a derivative thereof having greater than 72% sequence similarity, preferably 80% sequence similarity and more preferably 90% sequence similarity thereto.

According to yet another embodiment of the invention, a method of transforming a suitable microorganism with DNA encoding an amino acid sequence according to the invention is provided.

In an especially preferred embodiment of the present invention, the cellulase is a cellulase derived from Bacillus sp. CBS 669.93 having a calculated molecular weight of approximately 63 kD. The approximately 63 kD cellulase has a calculated isoelectric point of about 5 and a pH optimum on CMC of about 6 at 40° C. and 60° C.

BRIEF DESCRIPTION OF THE FIGURES

FIG. 1 shows the pH profile activity of an approximately 63 kD cellulase derived from CBS 669.93 at 40° C. and 60° C.

FIGS. 2A–2C show the DNA sequence (SEQ ID NO:2) and corresponding amino acid sequence (SEQ ID NO:1) of an approximately 63 kD cellulase derived from CBS 669.93 with the leader peptide sequence underlined, which upon secretion is cleaved to yield the mature enzyme.

DETAILED DESCRIPTION OF THE INVENTION

"Derivative" is intended to indicate a protein which is derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme according to the present invention) and which peptides retain a characteristic enzyme nature of the precursor enzyme but which have altered properties in some specific aspect. For example, an altered cellulase may have an increased pH optimum or increased temperature resistance but will retain its characteristic cellulolytic activity. Derivatives also include chemical modifications of amino acid residues within the enzyme molecule.

A cellulase is "obtainable from" Bacillus 668.93 if such cellulase has an amino acid sequence which corresponds to the amino acid sequence of a cellulase which may be obtained from that organism. Thus cellulase with an identical amino acid sequence to the 63 kD cellulase of the invention derived from a different Bacillus would be "obtainable from" Bacillus 669.93.

"Host cell" means a cell which has the capacity to act as a host and expression vehicle for a recombinant DNA vector according to the present invention. In a preferred embodiment according to the present invention, "host cell" means the cells of Bacillus.

"DNA construct" or "DNA vector" means a nucleotide sequence which comprises one or more DNA fragments encoding any of the novel cellulases or cellulase derivatives described above.

In a preferred embodiment, the cellulase is obtainable from the Centraal Bureau voor Schimmelcultures, Baam, the Netherlands through microorganism deposition number CBS 669.93 (described in application PCT/EP94/04312), deposited under the Budapest Convention on Dec. 23, 1993. As used herein, the deposited species will be referred to as CBS 669.93. In a more preferred embodiment, the cellulase of the invention is an approximately 63 kD cellulase (calculated on the basis of amino acid sequence of the mature protein) derived from CBS 669.93 (referred to herein as the "63 kD Cellulase"). The approximately 63 kD cellulase has a calculated pI for the mature protein of about 5 and a pH optimum on CMC at 40° C. and 60° C. of about 6.

The gene encoding the amino acid sequence of the approximately 63 kD cellulase was analyzed by comparison with the accessible sequence data in various libraries (GenBank, Swiss-Prot, EMBL and PIR) using the of CAOS/CAMM Center, University of Nijmegen, Holland. A search of databases for a comparison of the cellulase encoded by the DNA sequence of the present invention with cellulases encoded by published or known cellulase gene sequences revealed that the greatest amount of amino acid identity was found in the cellulase CelB of *Bacillus lautus*.

The approximately 63 kD cellulase was shown to be 58% identical in sequence and 72% similar in sequence using the TFastA program as described by Pearson & Lipman, Proc. Nat. Acad. Sci., vol. 85, pp. 2444–2448 (1988). The TFastA Data Searching Program is commercially available in the Sequence Analysis Software Package Version 6.0 (Genetic Computer Group, Univ. Wisconsin Biotechnology Center, Madison, Wis. 53705). The sequence of *Bacillus lautus* is found in Jorgensen et al., Gene, vol. 93, pp. 55–60 (1990). Thus, the present invention encompasses a cellulase which has an amino acid sequence according to that in FIGS. 2A–2C (SEQ ID NO:1) or a derivative thereof having greater than 58% sequence identity, preferably greater than 80% sequence identity and most preferably greater than 90% sequence identity thereto. The present invention further encompasses a cellulase which has an amino acid sequence having greater than 72% sequence similarity, preferably greater than 80% sequence similarity and most preferably greater than 90% sequence similarity to the amino acid sequence according to FIGS. 2A–2C (SEQ ID NO:1).

The present invention also discloses a process for the production of the cellulase. In one embodiment, the cellulase may be produced by cultivating a suitable organism, e.g., Bacillus sp. CBS 669.93, under conditions so as to produce the cellulase. Preferably, such conditions include those generally suggested for the cultivation of Bacillus to maximize cellulase production and include the use of a cellulose derived substrate as an energy source in combination with necessary salts, ions and other well known ingredients. Generally, the medium used to cultivate the cells may be any conventional medium suitable for growing bacteria. The cells may be cultivated under aerobic conditions in a nutrient medium containing assimilable carbon and nitrogen together with other essential nutrients. Suitable carbon sources are carbohydrates such as sucrose, glucose and starch, or carbohydrate containing materials such as cereal grain, malt, rice and sorghum. The carbohydrate concentration incorporated in the medium may vary widely, e.g., up to 25% and down to 1–5%, but usually 8–10% will be suitable, the percentages being calculated as equivalents of glucose. The nitrogen source in the nutrient medium may be of inorganic and/or organic nature. Suitable inorganic nitrogen sources are nitrates and ammonium salts. Among the organic nitrogen sources used regularly in fermentation processes involving the cultivation of bacteria are soybean meal, cotton seed meal, peanut meal, casein, corn, corn steep liquor, yeast extract, urea and albumin. In addition, the nutrient medium should also contain standard trace substances.

The cellulase may be recovered from the medium by conventional procedures including separating the cells from the medium by centrifugation or filtration, if necessary after disruption of the cells, precipitating the proteinaceous components of the supernatant or filtrate by means of a salt, e.g., ammonium sulfate, followed by purification by a variety of chromatographic procedures, e.g., ion exchange chromatography, affinity chromatography or similar art recognized procedures. For the production of the alkaline cellulase according to the invention, it is preferred to cultivate under alkaline conditions using media containing a cellulose based energy source.

Preferably, the cellulase according to the present invention is produced utilizing genetic engineering techniques by transforming a suitable host cell with a gene encoding the cellulase and expressing under conditions appropriate for host cell growth and cellulase expression. As a first step, the chromosomal DNA may be obtained from the donor bacterial strain by the method of Saito and Miura (Saito & Miura, Biochim. Biophys. Acta., vol. 72, pp. 619 (1963)) or by a similar method. Restriction enzyme deavage of the chromosomal DNA thus obtained gives DNA fragments containing the alkaline cellulase gene. For this purpose, any restriction enzyme may be used provided that it does not cleave the region of said gene. In the alternative, a restriction enzyme may be used which cleaves the gene, using however, a reduced enzyme concentration or incubation time to permit only partial digestion. A preferred restriction endonuclease is Sau3A. From the resulting digestion mixture, suitable fragments (4–10 kb) may be isolated and used to transform a suitable host cell with a DNA construct, e.g., with a DNA construct including the approximately 9 kb DNA fragment encoding the 63 kD cellulase according to the invention in combination with a suitable vector sequence.

The gene encoding the cellulase of the present invention can be cloned using λ-phage (expression) vectors and *E. coli* host cells. (Alternatively PCR cloning using consensus primers designed on conserved domains may be used). Applicants have discovered that transformation of the gene encoding the cellulase of the present invention and expression in E. coli results in an active protein. After a first cloning step in E. coli, a cellulase gene according to the present invention can be transferred to a more preferred industrial expression host such as Bacillus or Streptomyces species, a filamentous fungus such as Aspergillus or Trichoderma, or a yeast such as Saccharomyces. High level expression and secretion obtainable in these host organisms allows accumulation of the cellulase in the fermentation medium from which it can subsequently be recovered.

Preferably, the expression host cell comprises a Bacillus sp., more preferably *Bacillus licheniformis* or *Bacillus subtilis*. In an especially preferred embodiment, the transformation host is deleted for protease genes to ensure that the product cellulase is not subject to proteolysis in the fermentation broth or concentrates thereof. A preferred general transformation and expression protocol for protease deleted Bacillus strains is provided in Ferrari et al., U.S. Pat. No. 5,264,366, incorporated herein by reference. Also preferably, the fermentation of the transformed Bacillus host is conducted at a pH of about 6.9. Transformation and expression in Aspergillus is described in, for example, Berka et al., U.S. Pat. No. 5,364,770, incorporated herein by reference. A preferred promoter when the transformation host cell is Bacillus is the aprE promoter.

The instant approximately 63 kD cellulase derived from CBS 669.93 has been shown to be useful in buffer systems comprising glycine, ammonium acetate, borax and/or tris. This cellulase has also been found to be activated on CMC by the presence of magnesium and inhibited by the presence of calcium. A proportion of magnesium to calcium of about 250 ppm: 750 ppm has also been found to result in an activity benefit.

According to the present invention, the cellulase compositions described above may be employed in detergent compositions according to art-recognized methods of utilizing cellulases in detergents. The excellent activity of the instant cellulase at alkaline pH should result in the present cellulase being especially useful in high pH detergents.

The invention will be explained in more detail in the following examples which are provided for illustrative purposes and should not to be construed as limitative of the invention.

EXAMPLE 1
Screening And Isolation of Cellulase From Alkaline Soil And Water Samples Two methods were applied for the isolation of cellulase-producing microorganisms from alkaline soil and water samples. In one method, the soil and water samples were suspended in 0.85% saline solution and directly used in the carboxymethyl cellulose (CMC)-agar diffusion assay for detection of cellulase producing colonies. In a second method, the soil and water samples were enriched for cellulase containing strains by incubation in a cellulose containing liquid minimal medium or GAM-medium for 1 to 3 days at 40° C. Cultures that showed bacterial growth were analyzed for cellulase activity using the CMC-agar diffusion assay for detection of cellulase producing colonies. The CMC-agar diffusion assay and enrichment procedure utilized a minimal medium preparation at a pH of about 9.7 comprising 1% $KNO_3$, 0.1% yeast extract (Difco), 0.1% $KH_2PO_4$, 0.02% $MgSO_4.7H_2O$, 1% $Na_2CO_3$, 4% NaCl and 0.25% CMC (Sigma C-4888). For solidification 1.5% agar was added.

One of two procedures was used for the CMC-agar diffusion assay depending on whether colonies or liquid fractions were tested. For testing colonies, cell suspensions in 0.85% saline solution were plated on CMC-containing minimal medium. After incubation for 1 to 3 days at 40° C., the plates were replica plated and the parent plate was flooded with 0.1% Congo Red for 15 minutes. The plates were destained with 1M NaCl for 30 minutes. The strains that showed a clearing zone around the colony were isolated as potential cellulases producing microorganisms. Liquid fractions were assayed by pipetting 40 µl aliquots of enzyme solution or fermentation broth into wells punched out from a layer of 5 mm of minimal medium in a petri dish. After incubation for 16 hours at 40° C. cellulase activity was detected by Congo Red/NaCl treatment. The diameter of the clearing zone is a measure for the CMCase activity.

Strains which showed clearing zones using either of the two screening methods were selected for growing up and isolation of cellulase. The colonies were fermented in 25 milliliter GAM-medium in 100 milliliter shake flasks in an Incubator Shaker (New Brunswick Scientific, Edison, N.J., USA), at 250 r.p.m. at 40° C. for 72 hours. CMCase activity was determined in the culture broth at pH 9 and 40° C. to verify the presence of cellulase in the fermentation broth. The complex medium (GAM) used for enzyme production consisted of Peptone (Difco) 0.5%, Yeast extract (Difco) 0.5%, Glucose. $H_2O$ 1%, $KH_2PO_4$ 0.1%, $MgSO_4.7H_2O$ 0.02%, $Na_2CO_3$ 1%, NaCl 4%. The pH was adjusted to 9.5 with 4M HCl after which 1% CMC was added.

Utilizing the method described above, a cellulase producing microorganism was isolated which was further characterized as being a motile, long, thin rod-shaped bacterium, occurring in long chains and giving a thread-like appearance or, alternatively, in pairs of cells in a "v" form. The sub-terminal spores were ellipsoidal with a clear swelling of the sporangium. Colonies on GAM-agar appeared as a cream colored, circular, flat, smooth and shiny surfaced with a slightly irregular margin. Based on 16S rRNA sequence analysis, the microorganism was classified as species of the genus Bacillus. The organism is referred to herein as CBS 669.93 and is deposited in the Centraal Bureau voor Schimmelcultures, Baarn, The Netherlands under that accession number.

EXAMPLE 2
Isolation of DNA, Transformation and Expression of Cellulase

The alkaliphilic Bacilli strain CBS 669.93 was chosen as a donor strain for expression cloning in E. coli. Chromosomal DNA was isolated according to the method described by Saito & Miura, Biochim. Biophys. Acta., vol. 72, pp. 619–629 (1963).

The isolated chromosomal DNA was partially digested by the restriction enzyme Sau3A using serial diluted enzyme solutions, for one hour at 37° C. using React Buffers (Gibco BRL Life Technologies, Gaithersburg, Md., USA) under conditions recommended by the supplier. The digested DNA was fractionated by agarose gel electrophoresis and suitable fractions (4–10 kb) were isolated from the gel using QIAquick Gel Extraction Kit according to the protocol described by the supplier (QIAGEN Inc., Chatsworth, Calif., USA).

The Sau3A fragments of the chromosomal DNA were used to construct genomic gene libraries in a BamH1, digested CIAP treated ZAP Express vector according to the protocol described by the supplier (Stratagene Cloning Systems, La Jolla, Calif., USA). pBK-CMV phagmids, containing the cloned DNA inserts, were excised from the ZAP Express™ vector and transformed into E. coli strain XLOLR.

Recombinant clones were screened by agar diffusion as described by Wood et al., Meth. Enzym., vol. 160, pp. 59–74 (1988). Strains that showed clearing zones around the colony were isolated. The CMCase activity of the isolated recombinants was determined after fermentation for 48 hours in 4*YEP-medium consisting of Yeast Extract (Difco) 4%, peptone (Difco) 8%, lactose 0.2%, ampicillin 100 μg/ml. The recombinant protein was purified (Example 3) and the N-terminal amino acid sequence was determined to be the following:

Asn-Glu-Asp-Val-Lys-Thr-Leu-Asp-Ile-Gln    (SEQ ID: NO 3).

Plasmid DNA of the cellulase producing recombinant was isolated using a QIAprep Plasmid Kit according to the protocol described by the supplier (QIAGEN Inc.). The plasmid contained an approximately 9 kb insert of chromosomal DNA. The nucleotide sequence of a fragment of 2777 bp was determined using a set of degenerated oligonucleotides derived from the N-terminal amino acid sequence as a primer to locate the gene on the 9 kb insert. The 2777 bp fragment contained an open reading frame of 1746 bp from which a protein of 574 amino acids could be deduced. The nucleotide sequence of the gene (SEQ. ID. NO 2) coding for said cellulase and the deduced amino acid sequence (SEQ ID NO 1) of the isolated single cellulase is shown in FIGS. 2A–2C.

EXAMPLE 3
Purification of Cellulase

The cellulase producing clones from Example 2 were grown on a complex medium (4*YEP) consisting of Yeast Extract (Difco) 4%, Peptone (Difco) 8%, lactose 0.2%, 100 μg/ml ampicillin). The fermentation broth was separated from the culture liquid by centrifugation (8000 rpm). The cellulase in the supernatant was precipitated with ammonium sulphate (65% saturation). The precipitate was dissolved in 25 mM phosphate buffer pH 7+5 mM EDTA until a conductivity of 7 mS/cm was achieved. This solution was applied to a Q-Sepharose FF (diameter 5 cm, length 10 cm) Anion Exchange column, after which the column was washed with 25 mM phosphate buffer pH 7+5 mM EDTA until an absorbency of 0.2 AU. A gradient of 0 to 0.5 M NaCl in 25 mM phosphate pH 7 was applied to the column in 80 minutes followed by a gradient from 0.5 to 1 M NaCl in 10 minutes. Elution took place in the first gradient. After elution the column was cleaned (upflow) with 1 M NaOH and equilibrated again with 25 mM phosphate pH 7+5 mM EDTA. Depending on the elution profile, the obtained cellulase had a purity of up to about 80%.

EXAMPLE 4
Properties of Cellulase According to the Invention

To determine the pH/temperature profile of the approximately 63 kD cellulase according to the invention, the activity of the cellulase was measured on CMC at various pH and temperature values. A solution comprising the approximately 63 kD cellulase was combined in a buffer in diluted with 10 mM phosphate buffer (pH 7). (pH was controlled by using buffer comprising a mixture of 100 ml 1 M phosphoric acid, 100 ml citric acid and 600 ml distilled water having the pH adjusted to 4, 5, 6, 7, 8, 9 or 10 using 4 M NaOH, after which the mixture is filled to 1 L using distilled water). The enzyme solution was diluted until 0.05 U/ml measured at pH 7 and 40° C. Each buffer system was tested to ascertain the actual pH after mixing 0.5 ml Buffer, 0.5 ml substrate (1% CMC) and 0.1 ml 10 mM phosphate buffer. Actual pH for the pH 4, 5, 6, 7, 8, 9 and 10 solutions was 4.2, 5.2, 6.2, 7, 8, 8.7 and 9.9, respectively.

The results are illustrated in FIG. 1 showing the excellent alkaline activity of the cellulase. The slope of the calibration curve is dependent on the pH of the enzyme substrate mixture for that reason two glucose standards at each pH are taken (500 mg glucose. H2)/100 ml 10 and 25 times diluted.

Cellulase activity may be assayed using a modified PAHBAH method (Lever M. Anal. Biochem. 1972, 47, 273–279 and Lever M. Anal. Biochem. 1977, 81, 21–27) as follows. The pH/temperature profiles may be determined using a fixed enzyme concentration which fits in the linear range of the dose response profile measured at pH 7 and 40° C. This enzyme concentration may be used for the measurement of the activities under all other determined conditions. A test tube is filled with 250 μl 2.5% CMC in 50 mM glycine buffer pH 9 (CMC-low viscosity is purchased from Sigma) and 250 μl aliquots of the 63 kD cellulase, diluted in the appropriate buffer. The test tube is incubated for 30 minutes at 40° C. in a waterbath, whereafter 1.5 ml of a daily fresh prepared PAHBAH solution (1% PAHBAH in 100 ml 0.5 M NaOH with 100 ml bismuth solution (containing 48.5 g bismuth nitrate, 28.2 g potassium sodium tartrate and 12.0 g NaOH in 100 ml) is added. The mixture is heated at 70° C. for 10 minutes, after which it is cooled on ice for 2 minutes. The absorption is measured at 410 nm. To eliminate the background absorbance of the enzyme samples a control experiment is executed as follows: a tube with substrate is incubated under the same conditions as the test tube. After the incubation 1.5 ml PAHBAH and the enzyme preparation is added (in this order). One unit (U) is defined as the amount of enzyme producing 1 μmol of glucose from CMC equivalent determined as reducing sugars per minute per gram product.

I claim:

1. A cellulase composition obtainable from Bacillus sp. CBS 669.93 wherein said cellulase composition differs from the composition produced by wild type Bacillus sp. CBS 669.93.

2. A cellulase composition which comprises an amino acid sequence having a sequence identity of at least 80% to SEQ ID NO:1, wherein the sequence identity is determined according to TFASTA, as described in Pearson & Lipman, *Proc. Nat'l Acad. Sci. USA* 85:2444 (1988); and wherein said cellulase composition differs from the composition produced by wild type Bacillus sp. CBS 669.93.

3. The composition according to claim 2, wherein said cellulase has a sequence identity of at least 90% to SEQ. ID NO. 1.

4. A composition comprising DNA which encodes an amino acid sequence according to claim 2 or 3.

5. An expression vector comprising the DNA composition of claim 4.

6. A method of expressing a cellulase comprising:

(a) transforming a suitable microorganism with DNA encoding an amino acid sequence according to claim 2 or 3;

(b) preparing a fermentation broth containing said suitable microorganism under conditions suitable for expression of said DNA;

(c) maintaining said fermentation broth for a time and under conditions to permit the expression of a desired amount of said cellulase; and (d) collecting said fermentation broth which contains said cellulase.

7. A detergent composition comprising cellulase composition selected from the cellulase compositions of claims 1, 2 or 3.

8. A method of treating textiles comprising contacting said textile with a cellulase composition selected from the cellulase compositions of claims 1, 2 or 3.

9. A method of treating cellulose based pulp comprising contacting said cellulose based pulp with a cellulase composition selected from the cellulase compositions according to claims 1, 2 or 3.

* * * * *